(12) United States Patent
Sadhu (10) Patent No.: US 8,568,313 B2
(45) Date of Patent: Oct. 29, 2013

(54) USER WEARABLE PORTABLE COMMUNICATION DEVICE FOR COLLECTION AND TRANSMISSION OF PHYSIOLOGICAL DATA

(76) Inventor: Rajendra Padma Sadhu, Somerset, NJ (US)

( * ) Notice: Subject to any disclaimer, the term of this patent is extended or adjusted under 35 U.S.C. 154(b) by 0 days.

(21) Appl. No.: 13/105,925

(22) Filed: May 12, 2011

(65) Prior Publication Data

US 2012/0041278 A1 Feb. 16, 2012

Related U.S. Application Data (63) Continuation-in-part of application No. 12/722,554, filed on Mar. 12, 2010.

(51) Int. Cl.
*A61B 5/00* (2006.01)
(52) U.S. Cl.
USPC ........... 600/301; 600/453; 600/304; 600/372; 705/2; 705/3; 340/539.12; 709/230; 709/217
(58) Field of Classification Search
None
See application file for complete search history.

(56) References Cited

U.S. PATENT DOCUMENTS

| | | | | |
|---|---|---|---|---|
| 6,610,012 | B2 * | 8/2003 | Mault | 600/437 |
| 6,648,820 | B1 * | 11/2003 | Sarel | 600/300 |
| 7,006,408 | B2 * | 2/2006 | Chen | 368/10 |
| 8,005,691 | B2 * | 8/2011 | Kumar et al. | 705/3 |
| 8,301,232 | B2 * | 10/2012 | Albert et al. | 600/509 |
| 2004/0015079 | A1 * | 1/2004 | Berger et al. | 600/437 |
| 2005/0277872 | A1 * | 12/2005 | Colby et al. | 604/67 |
| 2007/0088521 | A1 * | 4/2007 | Shmueli et al. | 702/127 |
| 2007/0130287 | A1 * | 6/2007 | Kumar et al. | 709/217 |
| 2008/0001735 | A1 * | 1/2008 | Tran | 340/539.22 |
| 2008/0089182 | A1 * | 4/2008 | Scheybal | 368/10 |
| 2008/0146277 | A1 * | 6/2008 | Anglin et al. | 455/556.1 |
| 2008/0300010 | A1 * | 12/2008 | Border et al. | 455/556.1 |
| 2009/0231960 | A1 * | 9/2009 | Hutcheson | 368/10 |
| 2010/0191119 | A1 * | 7/2010 | Muthya et al. | 600/453 |
| 2010/0321899 | A1 * | 12/2010 | Vossoughi et al. | 361/728 |
| 2011/0218436 | A1 * | 9/2011 | Dewey et al. | 600/443 |
| 2011/0270631 | A1 * | 11/2011 | Cambray et al. | 705/3 |

* cited by examiner

*Primary Examiner* — Bill Thomson
*Assistant Examiner* — Marie Archer
(74) *Attorney, Agent, or Firm* — Maier & Maier, PLLC (57) ABSTRACT

A user wearable portable communication device and a method for collecting and transmitting a plurality of physiological parameters to a remote monitoring center are disclosed. The portable communication device includes a provision for enabling the user to establish a video conference, a fall detection module in conjunction with an accelerometer recognizes a placement of the portable communication device, a home automation module for enabling the user to remotely operate multiple electronic devices, an acknowledgment acceptance module for receiving the acknowledgment, a physiological data collecting module communicatively coupled to a fetal doppler module for monitoring and transmitting the physiological parameters associated with a child, multiple preprogrammed contact numbers for enabling the user to establish a communication, a subscriber identity module for enabling the user establish a communication and data transmission between the portable communication device and the remote monitoring center.

9 Claims, 4 Drawing Sheets

USER WEARABLE PORTABLE COMMUNICATION DEVICE FOR COLLECTION AND TRANSMISSION OF PHYSIOLOGICAL DATA

CROSS REFERENCE OF RELATED APPLICATION

This is a Continuation-In-Part application of a non-provisional application having an application Ser. No. 12/722,554 and a filing date of Mar. 12, 2010.

TECHNICAL FIELD OF THE INVENTION

The present invention generally relates to a user wearable portable communication device. More particularly the present invention is related to a user wearable portable communication device for collecting and transmitting physiological parameters to a remote monitoring center.

BACKGROUND OF THE INVENTION

Generally, the number of users requiring the remote health care is increasing in the past few years. The remote health care systems use a variety of health care devices to continuously monitor the user in a non-invasive manner. But these types of health care devices are not portable and restricted to one geographical area.

Emergency health crises that require immediate attention have been a difficult problem to address regardless of the age of the person encountering a medical emergency situation. Conventionally, the panic button type devices interlink the user to the emergency response team via landline or mobile telephone. If the user is suddenly disabled during a sudden health crisis, such as in a heart attack or a serious fall situation, the panic-button type devices become useless. Further more if the person is able to press the button the person should be within the effective wireless transmission distance to the device that dials the telephone to report the emergency. The panic button type devices are not effective for the users when the users are in unconscious state or rendered incapacitated by a fall or other medical condition. Furthermore no vital information on the user's status like heart rate, blood pressure, breath rate, body temperature, oxygen level and the like will be transmitted to the response team to provide further medical assistance. Consequently, it is difficult for the response team to diagnose and provide treatment to the user.

Typically, the health monitoring systems should have an adjustable emergency alert level throughout a day for different levels of activity. The capacity to determine the location of the person, who requires immediate medical assistance, should be more effective, accurate and relevant to provide proper medical assistance. The global positioning systems (GPS) determine the location of the user when signals from multiple GPS satellites are received by the system. The GPS system fails to determine the location of the user when signals are not received from more than one satellite due to shielding by buildings or geographic features or improper antenna orientation. The conventional GPS tracking systems comprises multiple integrated circuit chips. Consequently the multiple integrated circuit chips consume more power compared to the single integrated circuit chips with the combined capabilities of the individual integrated circuit chips. Furthermore the conventional GPS receivers can determine the location of the user only when there is clear view of the sky within several feet of the GPS receiver's antenna.

Typically, many health care facilities perform the vital sign monitoring of the user only once in a week due to the time and money needed to perform these operations. If the user's vital signs are checked only once in a week, the declining health condition of the user is detected after the health condition is worsened. Furthermore this is eliminating the opportunity for early intervention. The user's physiological parameters such as pulse rate, heart beat rate, electrocardiogram (EKG), blood pressure, breathing rate, body temperature and the like should be measured and monitored continuously. Further the measured parameters and the location of the user should be transmitted to the central monitoring system to continuously monitor the physiological parameters of the user while simultaneously tracking the location of the user.

In light of the aforementioned limitations, there clearly exists a need for user wearable portable communication device for monitoring, receiving and analyzing the physiological parameters related to the user for providing remote health care services by communicating with a remote health care monitoring center through a communication network by receiving the location of the user through the communication network for providing emergency medical services.

BRIEF SUMMARY OF THE INVENTION

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In accordance with teachings of the present disclosure, a user wearable portable communication device and a method for collecting and transmitting a plurality of physiological parameters to a remote monitoring center are disclosed.

In accordance with teachings of the present disclosure, the present invention describes about a user wearable portable communication device for receiving a plurality of physiological parameters from a plurality of physiological data collecting devices.

Further purpose of the present invention is to transmit the plurality of physiological parameters from the user wearable portable communication device to a remote monitoring center for providing a remote health care services.

Another objective of the present invention is to enable a communication between an expectant and the remote monitoring center for monitoring and transmitting the physiological parameters associated with a child by utilizing a fetal doppler module.

Still another objective of the present invention is to track a current location of a user by utilizing a global positioning system communication network.

Other objective of the present invention, the portable communication device facilitates the user to remotely operate a plurality of electronic devices by utilizing a home automation module.

Further objective of the present invention, the portable communication device receives an acknowledgement of a plurality of reminders for preventing the repetition of the alarms.

Still further objective of the present invention is to facilitate the user to establish a video conference with the multiple health care providers present over the remote monitoring center. Still another objective of the present invention is to provide a plurality of preprogrammed contact number for facilitating the communication between the portable communication device and the remote monitoring center through a plurality of user controllable switches.

Further objective of the present invention is to recognize a placement of the portable communication device by a fall detection module operating in conjunction with the accelerometer.

Still further objective of the present invention, the user wearable portable communication device utilizes a short range communication for collecting data from the plurality of physiological devices and utilizes a long range communication for transmitting the collected data to the remote monitoring center.

Another purpose of the present invention provide emergency medical attention to the user by continuously monitoring the plurality of physiological parameters.

A user wearable portable communication device and a method for collecting and transmitting a plurality of physiological parameters to a remote monitoring center are disclosed. According to a first aspect of the present invention, the user wearable portable communication device includes at least one provision for enabling the user to establish a video conference with the plurality of health care providers present over the remote monitoring center. The communication with the remote monitoring center enabled through a communication network includes at least one of a global system for mobile communications, a general packet radio service, a wifi network. The at least one provision for enabling the user to establish a video conference with the plurality of health care providers includes at least one of a webcam, a video camera and the like.

According to the first aspect of the present invention, the user wearable portable communication device includes at least one fall detection module in conjunction with an accelerometer recognizes a placement of the portable communication device.

According to the first aspect of the present invention, the user wearable portable communication device includes at least one home automation module for enabling the user to remotely operate a plurality of electronic devices.

According to the first aspect of the present invention, the user wearable portable communication device includes at least one acknowledgment acceptance module for receiving the acknowledgment corresponding to a plurality of medical reminders.

According to the first aspect of the present invention, the user wearable portable communication device includes at least one physiological data collecting module communicatively coupled to at least one fetal doppler module for monitoring and transmitting the physiological parameters associated with a child to the plurality of health care providers present over the remote monitoring center. The at least one physiological data collecting module receives the physiological parameters over a short range communication network employing a set of communication protocols from a plurality of plurality of physiological data collecting devices. The set of communication protocols include at least one of a transmission control protocol/internet protocol, a hyper text transfer protocol and the like. The short range communication network includes at least one of a bluetooth network, a zigbee network and the like.

According to the first aspect of the present invention, the user wearable portable communication device includes a plurality of preprogrammed contact numbers for enabling the user to establish a communication with the plurality of health care providers.

According to the first aspect of the present invention, the user wearable portable communication device includes at least one subscriber identity module for enabling the user perform at least one of a step of establishing a communication between the portable communication device and the remote monitoring center, a step of data transmission between the portable communication device and the remote monitoring center and the like.

According to the first aspect of the present invention, the user wearable portable communication device further includes a location tracking module for tracking a current location of the user through at least one of an assisted global positioning system, a global positioning system and the like.

According to the first aspect of the present invention, the user wearable portable communication device further includes a universal serial bus provision for receiving the physiological parameters from the plurality of physiological data collecting devices.

According to a second aspect of the present invention, a method adapted for collecting and transmitting a plurality of physiological parameters from a user wearable portable communication device to a remote monitoring center is disclosed. The method adapted for collecting and transmitting a plurality of physiological parameters from a user wearable portable communication device to a remote monitoring center includes facilitating a video conference between a user and a plurality of health care providers present over the remote monitoring center by using at least one provision.

According to the second aspect of the present invention, the method adapted for collecting and transmitting a plurality of physiological parameters from a user wearable portable communication device to a remote monitoring center includes detecting a placement of the portable communication device by using at least one fall detection module in conjunction with an accelerometer.

According to the second aspect of the present invention, the method adapted for collecting and transmitting a plurality of physiological parameters from a user wearable portable communication device to a remote monitoring center includes remotely operating a plurality of electronic devices by using at least one home automation module.

According to the second aspect of the present invention, the method adapted for collecting and transmitting a plurality of physiological parameters from a user wearable portable communication device to a remote monitoring center includes receiving the acknowledgment of the plurality of medical reminders by using at least one acknowledgment acceptance module.

According to the second aspect of the present invention, the method adapted for collecting and transmitting a plurality of physiological parameters from a user wearable portable communication device to a remote monitoring center includes monitoring and transmitting the physiological parameters associated with a child to the plurality of health care providers present over the remote monitoring center by utilizing at least one physiological data collecting module communicatively coupled to at least one fetal doppler module.

According to the second aspect of the present invention, the method adapted for collecting and transmitting a plurality of physiological parameters from a user wearable portable communication device to a remote monitoring center includes enabling the user to establish a communication with the plurality of health care providers by utilizing a plurality of preprogrammed contact numbers. The plurality of physiological parameters from the plurality of physiological data collecting devices of the user collected through a short range communication. The plurality of preprogrammed contact numbers enables the user to establish a communication with the plurality of health care providers present over the remote monitoring center.

According to the second aspect of the present invention, the method adapted for collecting and transmitting a plurality of physiological parameters from a user wearable portable communication device to a remote monitoring center includes establishing a communication between the portable communication device and the remote monitoring center through at least one subscriber identity module for enabling at least one of a voice based communication, a data transmission and the like.

According to the second aspect of the present invention, the method adapted for collecting and transmitting a plurality of physiological parameters from a user wearable portable communication device to a remote monitoring center further includes employing a set of communication protocols for enabling a communication between the plurality of physiological data collecting devices and the portable communication device.

BRIEF DESCRIPTION OF THE DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein.

DETAILED DESCRIPTION OF THE INVENTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

Exemplary embodiments of the present invention are directed towards A user wearable portable communication device and a method for collecting and transmitting a plurality of physiological parameters to a remote monitoring center are disclosed. According to the first aspect of a present invention, the user wearable portable communication device includes at least one provision for enabling the user to establish a video conference with the plurality of health care providers present over the remote monitoring center. The communication with the remote monitoring center enabled through a communication network includes at least one of a global system for mobile communications, a general packet radio service, a wifi network. The at least one provision for enabling the user to establish a video conference with the plurality of health care providers includes at least one of a webcam, a video camera and the like.

According to the first aspect of the present invention, the user wearable portable communication device includes at least one fall detection module in conjunction with an accelerometer recognizes a placement of the portable communication device.

According to the first aspect of the present invention, the user wearable portable communication device includes at least one home automation module for enabling the user to remotely operate a plurality of electronic devices.

According to the first aspect of the present invention, the user wearable portable communication device includes at least one acknowledgment acceptance module for receiving the acknowledgment corresponding to a plurality of medical reminders.

According to the first aspect of the present invention, the user wearable portable communication device includes at least one physiological data collecting module communicatively coupled to at least one fetal doppler module for monitoring and transmitting the physiological parameters associated with a child to the plurality of health care providers present over the remote monitoring center. The at least one physiological data collecting module receives the physiological parameters over a short range communication network employing a set of communication protocols from a plurality of plurality of physiological data collecting devices. The set of communication protocols include at least one of a transmission control protocol/internet protocol, a hyper text transfer protocol and the like. The short range communication network includes at least one of a bluetooth network, a zigbee network and the like.

According to the first aspect of the present invention, the user wearable portable communication device includes a plurality of preprogrammed contact numbers for enabling the user to establish a communication with the plurality of health care providers.

According to the first aspect of the present invention, the user wearable portable communication device includes at least one subscriber identity module for enabling the user perform at least one of a step of establishing a communication between the portable communication device and the remote monitoring center, a step of data transmission between the portable communication device and the remote monitoring center and the like.

According to the first aspect of the present invention, the user wearable portable communication device further includes a location tracking module for tracking a current location of the user through at least one of an assisted global positioning system, a global positioning system and the like.

According to the first aspect of the present invention, the user wearable portable communication device further includes a universal serial bus provision for receiving the physiological parameters from the plurality of physiological data collecting devices.

According to a second aspect of the present invention, a method adapted for collecting and transmitting a plurality of physiological parameters from a user wearable portable communication device to a remote monitoring center is disclosed. The method adapted for collecting and transmitting a plurality of physiological parameters from a user wearable portable communication device to a remote monitoring center includes facilitating a video conference between a user and a plurality of health care providers present over the remote monitoring center by using at least one provision.

According to the second aspect of the present invention, the method adapted for collecting and transmitting a plurality of physiological parameters from a user wearable portable communication device to a remote monitoring center includes detecting a placement of the portable communication device by using at least one fall detection module in conjunction with an accelerometer.

According to the second aspect of the present invention, the method adapted for collecting and transmitting a plurality of physiological parameters from a user wearable portable communication device to a remote monitoring center includes remotely operating a plurality of electronic devices by using at least one home automation module.

According to the second aspect of the present invention, the method adapted for collecting and transmitting a plurality of physiological parameters from a user wearable portable communication device to a remote monitoring center includes receiving the acknowledgment of the plurality of medical reminders by using at least one acknowledgment acceptance module.

According to the second aspect of the present invention, the method adapted for collecting and transmitting a plurality of physiological parameters from a user wearable portable communication device to a remote monitoring center includes monitoring and transmitting the physiological parameters associated with a child to the plurality of health care providers present over the remote monitoring center by utilizing at least one physiological data collecting module communicatively coupled to at least one fetal doppler module.

According to the second aspect of the present invention, the method adapted for collecting and transmitting a plurality of physiological parameters from a user wearable portable communication device to a remote monitoring center includes enabling the user to establish a communication with the plurality of health care providers by utilizing a plurality of preprogrammed contact numbers. The plurality of physiological parameters from the plurality of physiological data collecting devices of the user collected through a short range communication. The plurality of preprogrammed contact numbers enables the user to establish a communication with the plurality of health care providers present over the remote monitoring center.

According to the second aspect of the present invention, the method adapted for collecting and transmitting a plurality of physiological parameters from a user wearable portable communication device to a remote monitoring center includes establishing a communication between the portable communication device and the remote monitoring center through at least one subscriber identity module for enabling at least one of a voice based communication, a data transmission and the like.

According to the second aspect of the present invention, the method adapted for collecting and transmitting a plurality of physiological parameters from a user wearable portable communication device to a remote monitoring center further includes employing a set of communication protocols for enabling a communication between the plurality of physiological data collecting devices and the portable communication device.

Figure 1A:
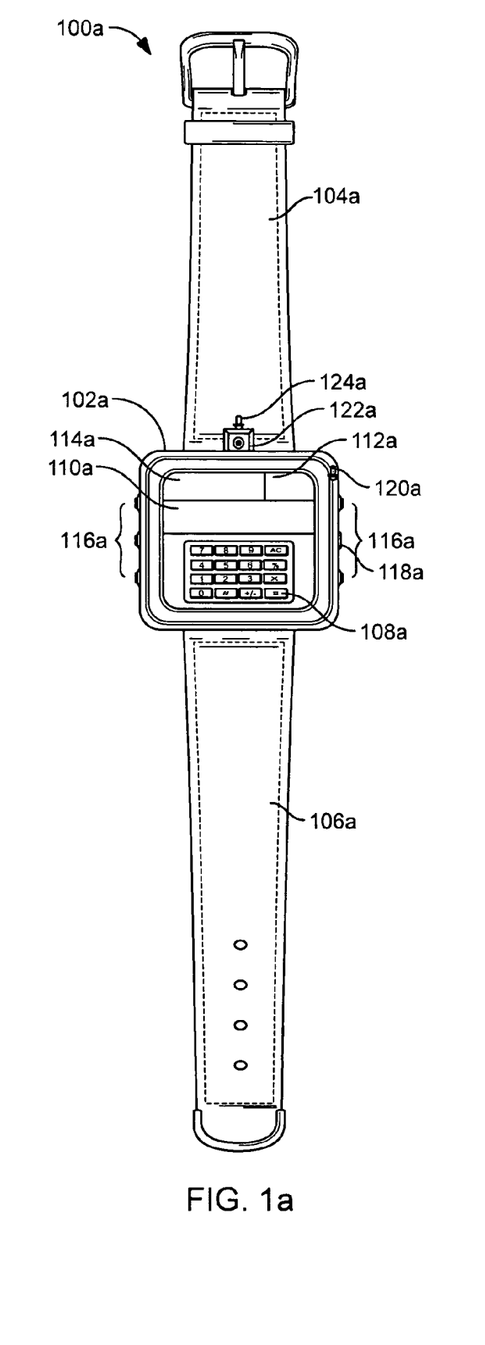
FIG. 1a is a diagram depicting a user wearable portable communication device with a keypad.

Referring to FIG. 1a is a diagram 100a depicting a user wearable portable communication device with keypad. According to an exemplary embodiment of the present invention, the user wearable portable communication device includes a main housing 102a, a first strap 104a, a second strap 106a, a keypad 108a, a physiological parameter display 110a, a time display 112a, a date display 114a, multiple user controllable switches 116a, a universal serial bus provision 118a, a microphone 120a, a provision for video conference 122a and a holed provision 124a to use the wearable portable communication device as a pendent.

In accordance with an exemplary embodiment of the present invention, the main housing 102a of the user wearable portable communication device includes a keypad 108a for facilitating the user to establish a communication by dialing the plurality of numbers present on the keypad. The communication is enabled by a subscriber identity module (SIM) present in the portable communication device. The microphone 120a positioned on the main housing 102a of the portable communication device facilitates the voice based communication. The main housing 102a further includes physiological parameter display 110a for displaying the multiple physiological parameters of the user received from the multiple physiological data collecting devices. The multiple physiological parameters of the user includes a heart rate, a pulse rate, a body temperature, a body fat and weight, a blood sugar, a breath rate, other medical data and the like. The multiple physiological data collecting devices includes a chest belt, a blood pressure monitor, a body fat and weight scale, a blood sugar monitor and the like.

According to an exemplary embodiment of the present invention, the first strap 104a is attached to the first end of the main housing 102a and the second strap 106a is attached to the second end of the main housing 102a. The main housing 102a includes the time display 112a for displaying the time and the date display 114a for displaying the date. The display module simultaneously displays the measured physiological parameters, time and date. The display module is an organic light emitting diode (OLED) made with organic material for displaying the data according to a non limiting exemplary embodiment of the present invention. The main housing 102a includes a universal serial bus provision 118a for receiving the physiological parameters from the multiple physiological data collecting devices. Further the physiological parameters from the multiple physiological data collecting devices are transmitted to the portable communication device through a short range communication network. The short range communication network preferably includes but not limited to a blue tooth network, a zigbee network and the like.

In accordance with an exemplary embodiment of the present invention, the received physiological parameters are further transmitted from the portable communication device to the remote monitoring center through a long range communication network. The long range communication network preferably includes but not limited to a global system for mobile communications (GSM), a general packet radio service (GPRS), a wifi network and the like. The global system for mobile communications (GSM) further includes dual band and quad band for supporting multiple frequencies of data transmission. The portable communication device further utilizes a global positioning system (GPS) for tracking a current location of the user. By tracking the current location of the user, the multiple health care providers present over remote monitoring center provides an emergency medical assistance to the user.

According to an exemplary embodiment of the present invention, the main housing 102a further includes the multiple user controllable switches 116a for enabling the user to establish a voice based communicative interaction with the multiple health care providers present over the remote monitoring center. The multiple user controllable switches 116a enable the user to establish the communication by utilizing multiple preprogrammed contact numbers stored in the portable communication device along with the microphone 120a. A holed provision 124a fastened to the main housing allows the user to wear the portable communication device as a pendent. The provision 122a for video enables the users to establish a video conference with the multiple health care providers present over the remote monitoring center. The provision 122a for video includes multiple embodiments preferably including but not limited to a web cam, a video camera, a digital camera and the like. Further the portable communication device enables the user remotely operate the multiple electronic devices by utilizing a home automation module.

Figure 1B:
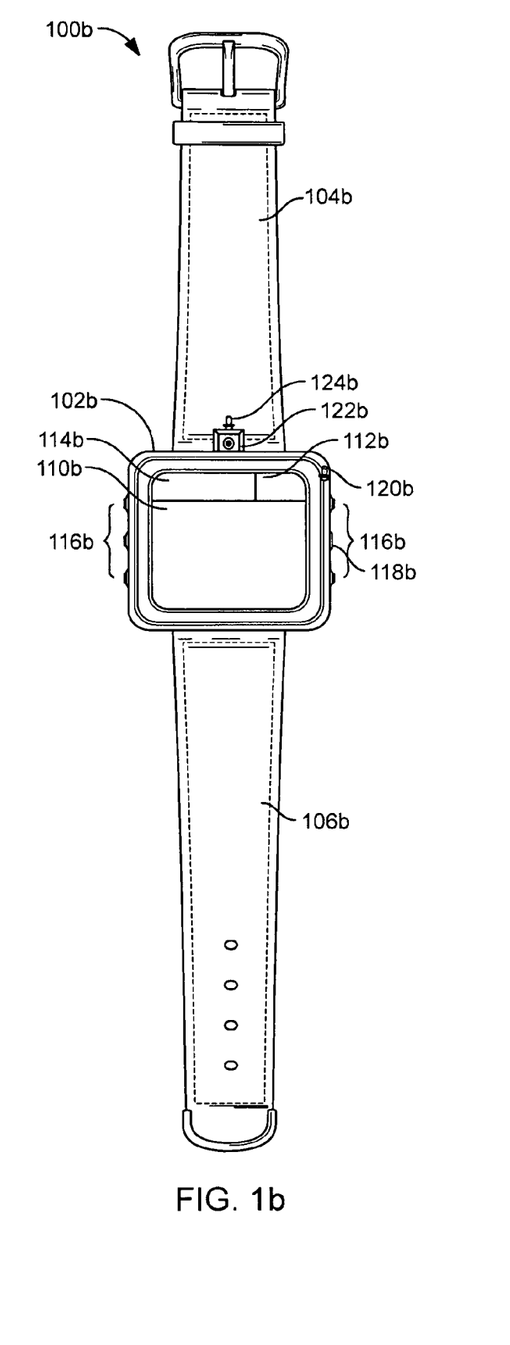
FIG. 1b is a diagram depicting a user wearable portable communication device without a keypad.

Referring to FIG. 1b is a diagram 100b depicting a user wearable portable communication device without a keypad. The portable communication device includes a main housing 102b, a first strap 104b, a second strap 106b, a physiological parameter display 110b, a time display 112b, a date display 114b, multiple user controllable switches 116b, a universal serial bus provision 118b, a microphone 120b, a provision for video conference 122b and a holed provision 124b to use the wearable portable communication device serving as a pendent.

In accordance with an exemplary embodiment of the present invention, the main housing 102b includes the physiological parameter display 110b for displaying the multiple physiological parameters received from the multiple physiological data collecting devices. The multiple physiological parameters of the user includes a heart rate, a pulse rate, a body temperature, a body fat and weight, a blood sugar, a breath rate, other medical data and the like. The multiple physiological data collecting devices includes a chest belt, a blood pressure monitor, a body fat and weight scale, a blood sugar monitor and the like. The time display 112b displays the time and the date display 114b displays the date.

According to an exemplary embodiment of the present invention, the multiple user controllable switches 116b enables the user to establish a voice based communication with the multiple health care providers present over the remote monitoring center by utilizing multiple preprogrammed contact numbers. The user is facilitated with the video conference by utilizing a provision 122b and the holed provision 124b positioned above the provision 122b for video enables the user to wear the portable communication device as a pendent in accordance with an exemplary embodiment of the present invention.

In accordance with an exemplary embodiment of the present invention, the first strap 104b is attached to the first end of the main housing 102b and the second strap 106b is attached to the second end of the main housing 102b. The first strap 104b and the second strap 106b enable the user to tie the portable communication device to the wrist of the user. The multiple user controllable switches 116b enable the user to establish a voice based communicative interaction with the multiple health care providers present over the remote monitoring center. The multiple user controllable switches 116b enable the user to establish the communication by utilizing multiple preprogrammed contact numbers stored in the portable communication device and the universal serial bus provision 118b of the portable communication device receives the multiple physiological parameters from the multiple physiological data collecting devices.

Figure 2:
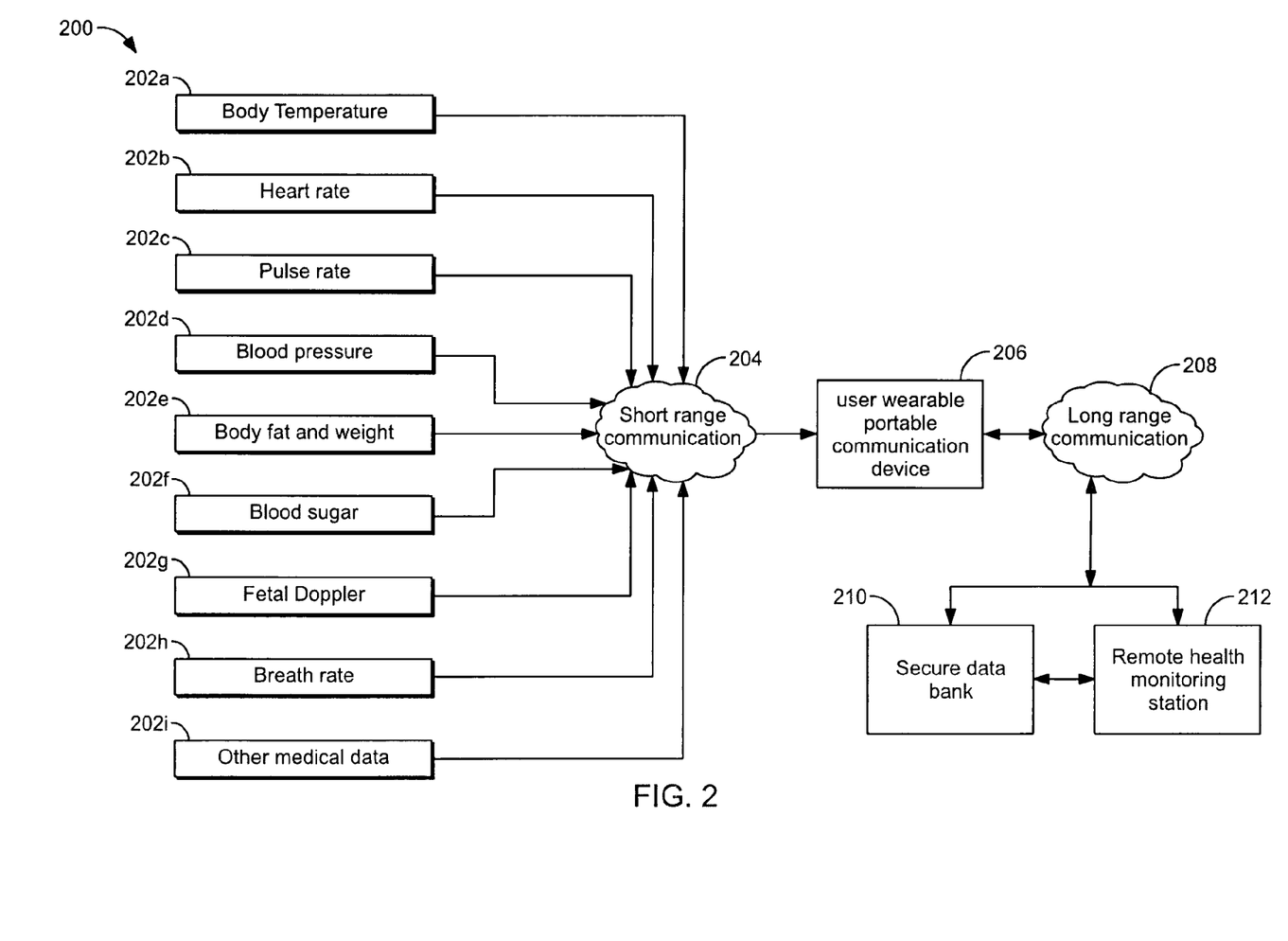
FIG. 2 is a diagram depicting an overview of a communication between a user wearable portable communication device and a remote monitoring center.

Referring to FIG. 2 is a diagram 200 depicting an overview of a communication between a user wearable portable communication device and a remote monitoring center. According to an exemplary embodiment of the present invention, the overview of the communication between the user wearable portable communication device and the remote monitoring center depicts multiple physiological parameters preferably including but not limited to a body temperature 202a, a heart rate 202b, a pulse rate 202c, a blood pressure 202d, a body fat and weight 202e, a blood sugar 202f, a fetal doppler 202g, a breath rate 202h and other medical data 202i received from the multiple physiological data collecting devices of the user, a short range communication network 204, a user wearable portable communication device 206, a long range communication network 208, a secure data bank 210 and a remote monitoring center 212.

According to an exemplary embodiment of the present invention, the multiple physiological parameters preferably including but not limited to the body temperature 202a, the heart rate 202b, the pulse rate 202c, the blood pressure 202d, the body fat and weight 202e, the blood sugar 202f, the fetal doppler 202g, the breath rate 202h and the other medical data 202i is received from the multiple physiological data collecting devices including a chest belt, a blood pressure monitor, a body fat and weight scale, a blood sugar monitor and the like. The multiple physiological parameters are received by the portable communication device by utilizing a short range communication network 204. The short range communication network preferably includes but not limited to a bluetooth network, a zigbee network and the like. The portable communication device receives the multiple physiological parameters from the multiple physiological data collecting devices during predefined regular intervals. In emergency situations the portable communication device facilitates the user to establish a communication with multiple health care providers present over the remote monitoring center by dialing the multiple preprogrammed contact number stored in the portable communication device by utilizing the multiple user controllable switches. Further the user is also facilitated with a provision to establish a video conference with the multiple health care providers present over the remote monitoring center. The portable communication device communicatively coupled with the fetal doppler for monitoring the physiological parameters of the child and transfers the monitored parameters to the remote monitoring center.

In accordance with an exemplary embodiment of the present invention, after receiving the multiple physiological parameters from the multiple physiological data collecting devices by utilizing the short range communication network, the portable communication device further transmits the collected physiological parameters to the remote monitoring station 212 through the long range communication network 208 for storing the multiple physiological parameters in the secure data bank 210. The long range communication network preferably includes but not limited to a global system for mobile communications (GSM), a general packet radio service (GPRS), a wifi network and the like. The portable communication device 206 further utilizes the global positioning system (GSM) for tracking the current location of the user.

According to an exemplary embodiment of the present invention, the multiple health care providers present over the remote monitoring center 212 receives the data transmitted by the portable communication device 206, stores the data in the secure databank, analyzes the received data and transmits the feed back to the portable communication device of the user. Depending upon the data received from the portable communication device 206, the multiple health care providers present over the remote monitoring center provides the assistance to the user.

Figure 3:
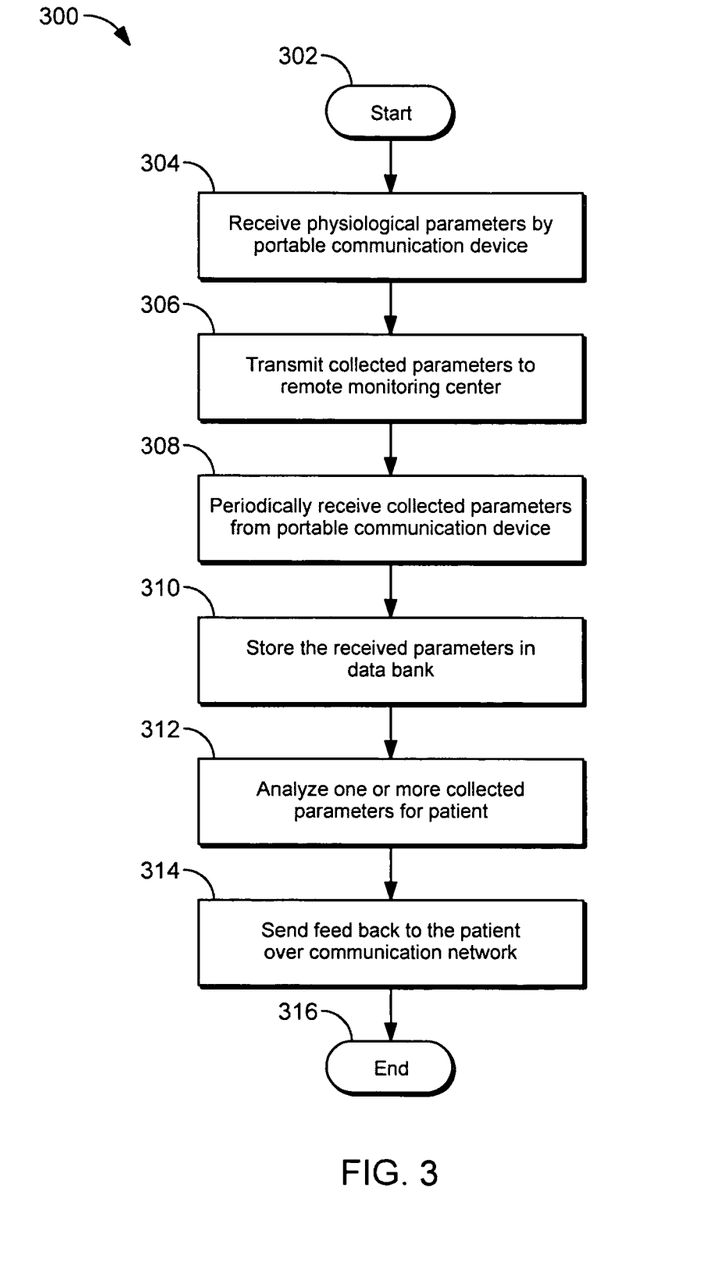
FIG. 3 is a flow diagram illustrating a method of communication between a user wearable portable communication device and a remote health care monitoring center.

Referring to FIG. 3 is a flow diagram 300 illustrating a method of communication between a user wearable portable communication device and a remote monitoring center. According to an exemplary embodiment of the present invention, the method of communication between the user wearable portable communication device and the remote monitoring center starts at step 302.

From step 302, the flow diagram 300 continues with step 304 which describes about a portable communication device receiving multiple physiological parameters from the multiple physiological data collecting devices. The multiple physiological parameters preferably includes but not limited to a heart rate, a pulse rate, a body temperature, a body fat and weight, a blood sugar, a breath rate, other medical data and the like. The multiple physiological data collecting devices includes a chest belt, a blood pressure monitor, a body fat and weight scale, a blood sugar monitor and the like. The portable communication device receives the multiple physiological parameters from the multiple physiological data collecting devices by utilizing a short range communication network. The short range communication network preferably includes but not limited to a bluetooth network, a zigbee network and the like.

From step 304, the flow diagram 300 continues with step 306 which describes about transmitting the multiple collected physiological parameters to a remote monitoring center through a long range communication network. The long range communication network preferably includes but not limited to a global system for mobile communications (GSM), a general packet radio service (GPRS), a wifi network and the like. The portable communication device further utilizes the global positioning system (GSM) for tracking the current location of the user.

From step 306, the flow diagram 300 continues with step 308 which describes about the remote monitoring center periodically receiving the collected physiological parameters from the portable communication device. The remote monitoring center receives the multiple physiological parameters during regular intervals for continuously monitoring the user.

From step 308, the flow diagram 300 continues with step 310 which describes about storing the received multiple physiological parameters in the secure data bank. The data bank stored the multiple physiological parameters for maintaining a history of the medical records associated with the user while providing treatment to the user.

From step 310, the flow diagram 300 continues with step 312 which describes about analyzing the stored physiological parameters of the user. Analyzing the multiple physiological parameters by comparing the multiple physiological parameters stored in the secured databank enables the multiple health care providers to provide an effective medical assistance.

From step 312, the flow diagram 300 continues with step 314 which describes about transmitting a feed back to the portable communication device. The multiple health care providers present over the remote monitoring center transmits the feed back including medical assistance to the user based on the analyzed physiological parameters.

Finally, the flow diagram 300 depicting the method of communication between the user wearable portable communication device and the remote monitoring center ends at step 316.

Figure 4:
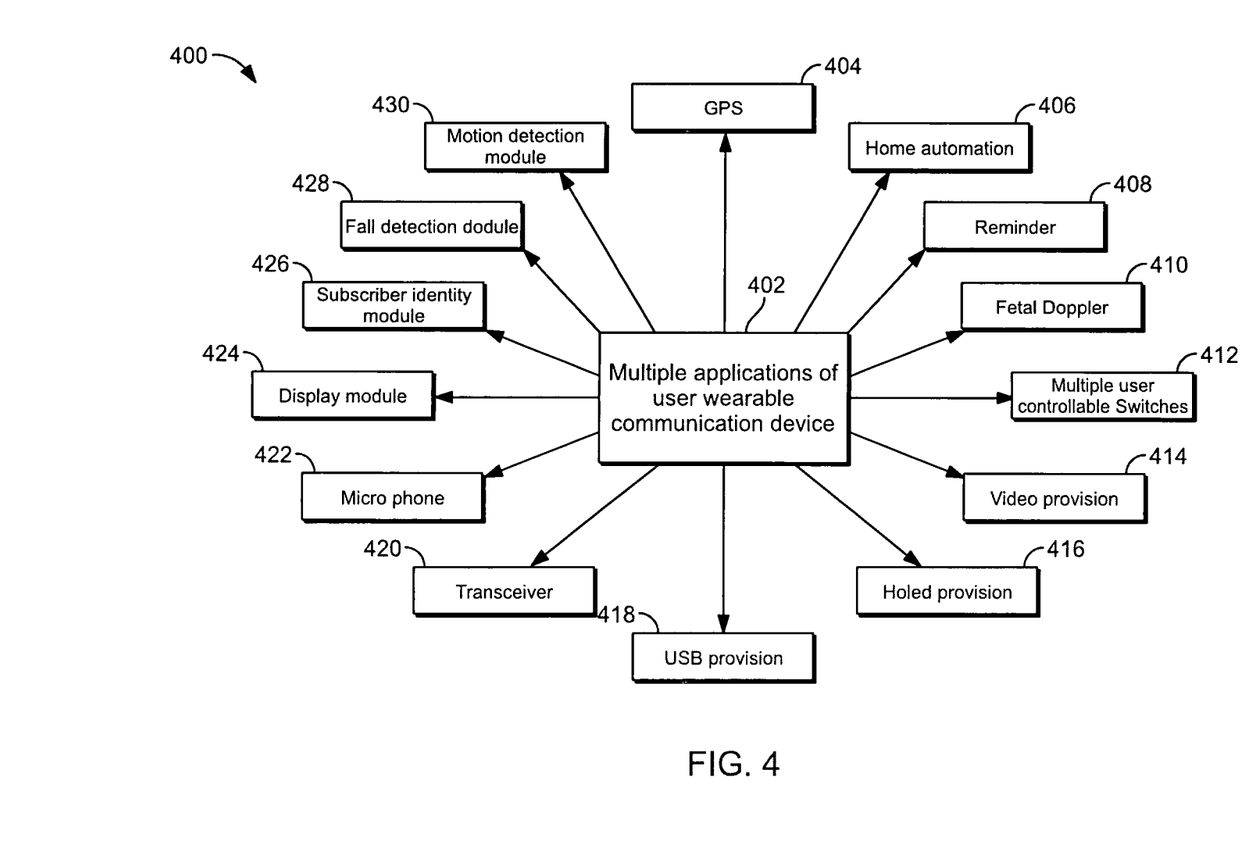
FIG. 4 is a diagram depicting an overview of multiple applications associated with a user wearable portable communication device.

Referring to FIG. 4 is a diagram 400 illustrating an overview of multiple applications associated with a user wearable portable communication device. According to an exemplary embodiment of the present invention, the overview of the multiple applications associated with the user wearable portable communication device 402 depicts a global positioning system (GPS) 404, an home automation 406, multiple reminders 408, a fetal dopplar 410, multiple user controllable switches 412, a provision 414 for enabling a video conference, a holed provision 416, a universal serial bus provision (USB) 418, a transceiver 420, a micro phone 422, a display module 424, a subscriber identity module (SIM) 426, a fall detection module 428, a motion detection module 430.

According to an exemplary embodiment of the present invention, the global positioning system (GSM) 404 in conjunction with a location tracking module of the portable communication device is used to track the current location of the user for providing emergency medical assistance. The home automation module 406 of the portable communication device is used to remotely operate multiple electronic devices located at home. The multiple electronic devices preferably includes but not limited to a air conditioner, a cooler, a fridge, a bulb, a fan, a woven and the like. The multiple reminders 408 enable the user to take the medication at proper time. The acknowledgement acceptance of the multiple reminders prevents the repetition of the alarms. The fetal doppler 410 communicatively coupled with the portable communication device enables the user monitor the physiological parameters of the child and transmits the measured parameters to the remote monitoring center.

In accordance with an exemplary embodiment of the present invention, the multiple user controllable switches 412 facilitates the user to establish a voice based communicative interaction with the multiple health care providers present over the remote monitoring center. The user controllable switches 412 along with the microphone 422 are used for establishing the voice based communication and also the multiple preprogrammed contact numbers are utilized for communicating with the multiple health care providers present over the remote monitoring center. The provision 414 enables the user to establish a video conference with the multiple health care providers present over the remote monitoring center.

According to a non limiting exemplary embodiment of the present invention, the holed provision 416 facilitates the user to wear the portable communication device as a pendent and the universal serial bus provision 418 of the portable communication device receives the multiple physiological parameters from the multiple physiological data collecting devices. The transceiver 420 enables the transmission and reception of the data between the portable communication device and the remote monitoring center. The display 424 module of the portable communication device displays the multiple physiological parameters of the user, time and date. Further the subscriber identity module (SIM) 426 facilitates the user to communicate with the multiple health acre providers and also to transmit the data to the remote monitoring center after receiving from the multiple physiological data collecting devices of the user.

In accordance with an exemplary embodiment of the present invention, the fall detecting module in conjunction with the accelerometer recognizes the placement of the portable communication device and the motion detecting module 430 identifies the movement of the portable communication device for reducing the power consumption.

While specific embodiments of the invention have been shown and described in detail to illustrate the inventive principles, it will be understood that the invention may be embodied otherwise without departing from such principles.

The invention claimed is:

1. A user wearable portable communication device for collecting and transmitting a plurality of physiological parameters to a remote monitoring center, comprising:
   at least one provision for enabling a user to establish a video conference with a plurality of health care providers present over the remote monitoring center;
   at least one accelerometer for fall detection;
   at least one physiological data collecting means communicatively coupled to at least one fetal Doppler module for monitoring and transmitting physiological parameters associated with a child to the plurality of health care providers over the remote monitoring center;
   a plurality of preprogrammed contact numbers for enabling the user to establish a communication with the plurality of health care providers; and
   at least one subscriber identity module for enabling the user to perform at least one of: a step of establishing a communication between the portable communication device and the remote monitoring center; and a step of data transmission between the portable communication device and the remote monitoring center;
   wherein the user wearable portable communication device is operable to remotely operate a plurality of electronic devices;
   wherein the at least one physiological data collection means receives the physiological parameters over a short range communication network employing a set of communication protocols from a plurality of physiological data collecting devices, and
   wherein the communication with the remote monitoring center is enabled through a long range communication network comprising at least one of:
   a global system for mobile communications;
   a general packet radio service; and
   a wifi network.

2. The portable communication device of claim 1 further comprising a location tracking module for tracking a current location of the user though at least one of:
   an assisted global positioning system; and
   a global positioning system.

3. The portable device of claim 1, wherein the set of communication protocols comprising at least one of a transmission control protocol/internet protocol; and
   a hyper text transfer protocol.

4. The portable communication device of claim 1, wherein the short range communication network comprising at least one of:
   a bluetooth network; and
   a zigbee network.

5. The portable communication device of claim 1 further comprising a universal serial bus provision for receiving the physiological parameters from the plurality of physiological data collecting devices.

6. The portable communication device of claim 1, wherein the at least one provision for enabling the user to establish a video conference with the plurality of health care providers comprising at least one of:
   a webcam; and
   a video camera.

7. A method adapted for collecting and transmitting a plurality of physiological parameters from a user wearable portable communication device to a remote monitoring center, comprising:
   facilitating a video conference between a user and a plurality of health care providers present over the remote monitoring center by using at least one of a webcam and a video camera;
   detecting a placement of the portable communication device by using at least one accelerometer;
   remotely operating a plurality of electronic devices from the user wearable portable communication device;
   monitoring and transmitting at least one physiological parameter associated with a child to the plurality of health care providers present over the remote monitoring center by utilizing at least one physiological data collecting means communicatively coupled to at least one fetal Doppler module;
   enabling the user to establish a communication with the plurality of health care providers by utilizing a plurality of preprogrammed contact numbers; and
   establishing a communication between the portable communication device and the remote monitoring center through at least one subscriber identity module for enabling at least one of:
   a voice based communication; and
   a data transmission;
   wherein the at least one physiological data collecting means receives the physiological parameters over a short range communication network employing a set of communication protocols from a plurality of physiological data collecting devices, and
   wherein the communication with the remote monitoring center is enabled through a long range communication network comprising at least one of:
   a global system for mobile communications;
   a general packet radio service; and
   a wifi network.

8. The method of claim 7 further comprising employing a set of communication protocols for enabling a communication between the plurality of physiological data collecting devices and the portable communication device.

9. The method of claim 7, wherein the plurality of preprogrammed contact numbers enables the user to establish a communication with the plurality of health care providers present over the remote monitoring center.

* * * * *